United States Patent
Bader

(10) Patent No.: US 8,329,075 B2
(45) Date of Patent: Dec. 11, 2012

(54) METHOD AND DEVICE FOR MONITORING, DOCUMENTING, AND/OR CONTROLLING AN INJECTION MOLDING MACHINE

(75) Inventor: Christopherus Bader, Neftenbach (CH)

(73) Assignee: Priamus System Technologies AG, Schaffhausen (CH)

( * ) Notice: Subject to any disclaimer, the term of this patent is extended or adjusted under 35 U.S.C. 154(b) by 54 days.

(21) Appl. No.: 12/679,036

(22) PCT Filed: Sep. 22, 2008

(86) PCT No.: PCT/EP2008/007978
§ 371 (c)(1),
(2), (4) Date: Jun. 4, 2010

(87) PCT Pub. No.: WO2009/040077
PCT Pub. Date: Apr. 2, 2009

(65) Prior Publication Data
US 2010/0252944 A1    Oct. 7, 2010

(30) Foreign Application Priority Data
Sep. 20, 2007 (DE) .......................... 10 2007 045 111

(51) Int. Cl.
*B29C 45/76* (2006.01)
*B29C 45/77* (2006.01)
*B29C 45/78* (2006.01)

(52) U.S. Cl. ....... 264/40.1; 264/40.5; 425/145; 425/149
(58) Field of Classification Search ................. 264/40.1, 264/40.5; 425/145, 149
See application file for complete search history.

(56) References Cited

U.S. PATENT DOCUMENTS

| | | | |
|---|---|---|---|
| 4,833,910 A | | 5/1989 | Kenmochi |
| 5,221,500 A | * | 6/1993 | Gent et al. .................. 264/40.1 |
| 6,019,917 A | * | 2/2000 | Ryckebusch et al. ........ 264/40.1 |
| 6,649,095 B2 | * | 11/2003 | Buja .......................... 264/40.6 |
| 2005/0089593 A1 | | 4/2005 | Wang et al. |
| 2009/0278274 A1 | | 11/2009 | Bader |

FOREIGN PATENT DOCUMENTS

| | | |
|---|---|---|
| DE | 2358911 | 6/1974 |
| DE | 10 2005 032367 | 1/2007 |
| JP | 6320587 | 11/1994 |
| JP | 10323874 | 12/1998 |

* cited by examiner

*Primary Examiner* — Jill Heitbrink
(74) *Attorney, Agent, or Firm* — Bachman & LaPointe, P.C.

(57) ABSTRACT

A method for monitoring, documenting, and/or controlling an injection molding machine (P) having an injection molding tool (1) into which a melt is introduced, wherein a viscosity of the melt in the injection molding tool (1) is determined directly.

16 Claims, 3 Drawing Sheets

METHOD AND DEVICE FOR MONITORING, DOCUMENTING, AND/OR CONTROLLING AN INJECTION MOLDING MACHINE

BACKGROUND OF THE INVENTION

The invention relates to a method for monitoring, documenting and/or controlling an injection molding machine having an injection mold into which a melt is introduced, the viscosity of the melt in the injection mold being ascertained directly by way of the respective quotients of shear stress and shear rate on the basis of pressure differences, the geometry of the cavity and the flow rate of the melt.

To keep a check on the consistency of plastic material, pasty compositions, emulsions and liquids, the viscosity is determined in dependence on the shear rate. The viscosity describes dynamic shear stresses caused by internal friction in moving liquids or in pasty compositions. The definition of viscosity is based on Newton's theory, which states that the shear stress is proportional to the shear rate. The proportionality factor is in this case referred to as viscosity (shear viscosity). The two terms shear stress and shear rate can be explained by the example of a liquid film of a thickness d which rests on one bounding surface and is moved on the other at a velocity v on account of the shear force acting on it. The shear stress corresponds to the shear force per unit area and the shear rate corresponds to the change in the velocity of displacement of one bounding surface in relation to the other divided by the distance between the two bounding surfaces.

In order to determine a relationship between the shear rate and the shear stress or the viscosity, viscosity measurements must be carried out for various shear rates. The viscosity can be determined by the Hagen/Poiseuille method by means of a capillary through which the liquid or composition to be investigated flows on account of a charging pressure. The shear stress and the shear rate, and consequently the viscosity, can be determined from the rate of flow, the charging pressure, the change in pressure along the capillary and the cross section of the capillary. Because the shear rate depends both on the charging pressure and on the cross section of the capillary, measurements for various shear rates can be carried out by changing these variables.

U.S. registered design 3,438,158 discloses, for example, determining the flow stress and the viscosity of a non-Newtonian fluid. This involves pumping the fluid through a pipe of known diameter at a known flow rate. By repeated measurement of the pressure differences or the pressure drop along a given length of pipe under different conditions in each case, the aforementioned rheological parameters can be determined.

DE 10 2005 032 367 A1 already discloses a method for monitoring and/or controlling the filling with melt of at least one cavity of an injection molding machine. According to this document, material or viscosity fluctuations can be indirectly ascertained, monitored and controlled, to be precise by analyzing the differences in the time for filling with the melt from cycle to cycle. Although such a method allows differences in viscosity to be detected, and possibly corrected, it cannot be used to ascertain a genuine viscosity profile in the physical unit of pascals per second (Pa s). But to be able to quantify a change in viscosity, it must be known in the genuine physical unit.

A further method for monitoring injection molding processes is shown by U.S. Pat. No. 4,833,910. For this purpose, two pressure sensors are positioned in the cavity at a known distance in the direction of flow of the melt. The viscosity is determined by way of the pressure difference ascertained in this way, the time difference, the radius of the channel and the distance between the two sensors.

In classical rheometry, the viscosity is ascertained as a quotient of shear stress and shear rate, usually for material determination in the laboratory. Serving for this purpose are so-called rheometers, which have a die and an exactly defined melt channel for ascertaining the viscosity, with a contrast here in comparison with an injection molding process in that isothermal conditions prevail. That is to say that both the metal die and the plastics melt are at the same temperature.

Serving for measurement in a rheometer are two melt pressure sensors (no mold internal pressure sensors), which are arranged a certain distance apart and measure the pressure drop over this distance. The shear stress can then be calculated on the basis of the geometry of the melt channel, which may be designed for example as a bore or as a rectangular channel, and on the basis of the pressure drop. In this case, the melt discharge through the die is forced out (extruded) at different rates or under different pressures, with the result that different pressure gradients ($\Delta p$) are obtained. Each individual pressure gradient produces a shear stress of its own, and consequently a value in the profile of a viscosity curve.

At the same time, the corresponding shear rate is calculated once again on the basis of the geometry of the melt channel and on the basis of the time that elapses while the melt passes from the first melt pressure sensor to the second melt pressure sensor.

Finally, there is also a more simple method than that for determining viscosities, one in which only one melt pressure sensor is used. It measures the pressure drop from the sensor to atmospheric pressure of 1 bar. In the case of this method, however, a computational correction must be made—the so-called "Bagley correction"—in order to compensate for run-out pressure losses. These run-out pressure losses occur when the melt leaves the channel into the open and expands. Otherwise, the further procedure corresponds to the method of a rheometer.

The object of the present invention is to monitor, and possibly control, an injection molding process under practical conditions.

SUMMARY OF THE INVENTION

The foregoing object is achieved by ascertaining the viscosity by at least one mold internal pressure sensor and/or at least one mold wall temperature sensor, the pressure difference of the pressure ascertained by the mold internal pressure sensor at it when the melt arrives and at the mold of the wall temperature sensor when the melt arrives being used for the shear stress and the time that the melt needs to pass from the mold internal pressure sensor to the mold wall temperature sensor being used for ascertaining the flow rate.

In accordance with the present invention, the method according to the invention can be realized in a simple manner, as provided by a first preferred exemplary embodiment, by the viscosity being ascertained on the basis of at least one mold internal pressure sensor and at least one mold wall temperature sensor. On the one hand, the pressure of the melt as it arrives at the mold internal pressure sensor is ascertained and on the other hand the pressure of the melt as it arrives at the mold wall temperature sensor is ascertained. The pressure loss corresponds here exactly to the pressure value that prevails at the time of a rise in temperature, with the result that a second pressure value is not required since the pressure difference between the atmospheric pressure and this value is assumed. To ascertain the shear stress, the time that the melt needs to pass between the two sensors is used.

It is expedient here if the mold internal pressure sensor is provided in the vicinity of the entry of the melt into the cavity and the mold wall temperature sensor is provided in the following course of the flow path or in the vicinity of the end of the flow path of the melt. If, for example, the mold wall temperature sensor is situated in the vicinity of the end of the flow path, it is also possible at the same time to switch over automatically to the so-called follow-up pressure, while however the method according to the invention likewise functions very well if the mold wall temperatures sensor is positioned anywhere in the course of the melt flow.

If in the present invention mention is made of the mold wall temperature sensor or the mold internal pressure sensor, this means that both sensors are preferably arranged in the inner wall or near the surface of the cavity, i.e. in the first case they come into contact with the melt directly, in the second case they are only separated from the melt by a thin web. However, other sensors by means of which the pressure differences and melt temperature can be determined may also be used.

It may be provided as an expedient second exemplary embodiment that the viscosity is ascertained only on the basis of at least one mold wall temperature sensor provided in the flow path of the melt in the region of the cavity, the pressure differences in the injection nozzle of the injection molding machine being used as a basis for determining the shear stresses and the distance between the entry of the melt into the cavity and the position of the mold wall temperature sensor being used for determining the shear rates. Here it is also possible to use the pressure differences in the hydraulic system of the injection molding machine or in the hot runner instead of the pressure differences in the injection nozzle. In this respect, the melt pressures correspond to the true pressure values, which do not have to be converted, while the hydraulic pressure has to be converted to true pressure values in accordance with the cross section of the hydraulic piston and the cross section of the screw cylinder that is used here for example.

The method with the hydraulic pressure measurement is relatively inexpensive, since, by contrast with melt pressure measurement in the machine nozzle or in the hot runner, no additional sensor has to be installed. On the other hand, however, this method is not quite as accurate because of the friction losses.

Finally, it is also possible that the pressure losses are ascertained during the injection phase of the melt on the basis of a force measurement, since, along with the classical hydraulic machines, also increasingly being used are electrical injection molding machines, which are used in particular because of the energy saving. Since not pressures but forces are measured here, the pressure loss during the injection phase can therefore also be advantageously ascertained indirectly by way of a force measurement. The ascertainment of the shear rates can then take place in the case of such a force measurement in a way analogous to the second exemplary embodiment, to be precise by measuring and evaluating the time over the flow path between the sprue of the part and the position of the mold wall temperature sensor.

It should once again be expressly pointed out that the present invention does not replace the rheometer. By contrast to determination of the viscosity with the rheometer, according to the present invention a permanent monitoring of the injection molding process takes place. A viscosity value is monitored only if it changes; that is if there is a response in the course of the process that resumes this viscosity value.

BRIEF DESCRIPTION OF THE DRAWINGS

Further details and advantages of the invention emerge from the following description of several exemplary embodiments and on the basis of the drawing, in which.

DETAILED DESCRIPTION

Figure 1:
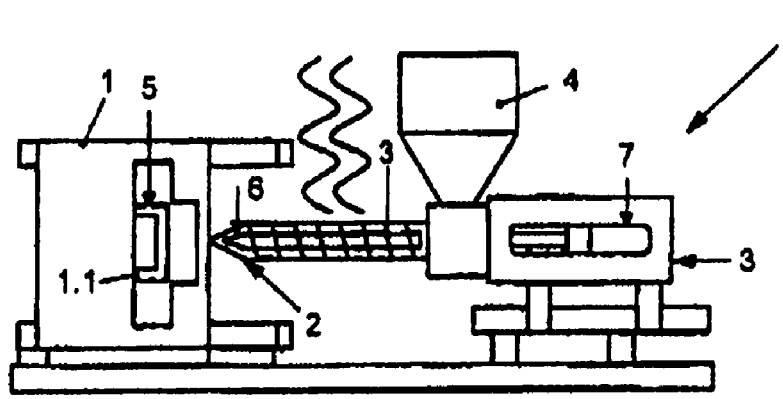
FIG. 1 shows a schematic side view of an injection molding machine according to the invention.

Schematically represented in FIG. 1 is an injection molding machine P, which in a known way comprises an injection mold 1 with a cavity 1.1 and a nozzle 2, through which a melt of plastics material is introduced into the cavity 1.1. The nozzle 2 is in turn connected to an extruder 3, to which a feed hopper 4 for plastics pellets or granules is assigned.

An arrow 5 indicates a measuring point for measuring the mold wall temperature—to be precise the inner wall temperature of the cavity, whereas an arrow 6 indicates that point where the melt pressure is measured in the region of the injection nozzle. Furthermore, an arrow 7 indicates that point where the hydraulic pressure is decisive as a measured variable.

Figure 2:
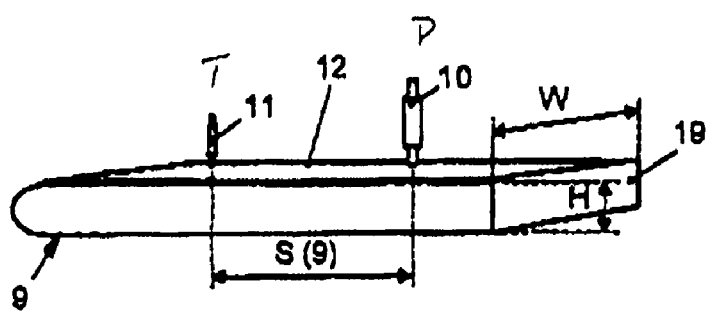
FIG. 2 shows as a first exemplary embodiment a basic construction of a cavity of an injection mold provided with measuring sensors, to be precise with a mold internal pressure sensor and a mold wall temperature sensor.

The basic construction of a cavity 9 represented in FIG. 2 as an exemplary embodiment, with a rectangular cross section and the dimensions of height H and width W for determining the respective geometry is only given by way of example. A mold internal pressure sensor 10 is provided near a sprue 19 and a mold wall temperature sensor 11 is provided at a distance S (9) therefrom; a mold wall indicated by 12 is "cold" and the interior of the cavity 9 during filling with the melt is "warm".

Figure 3:
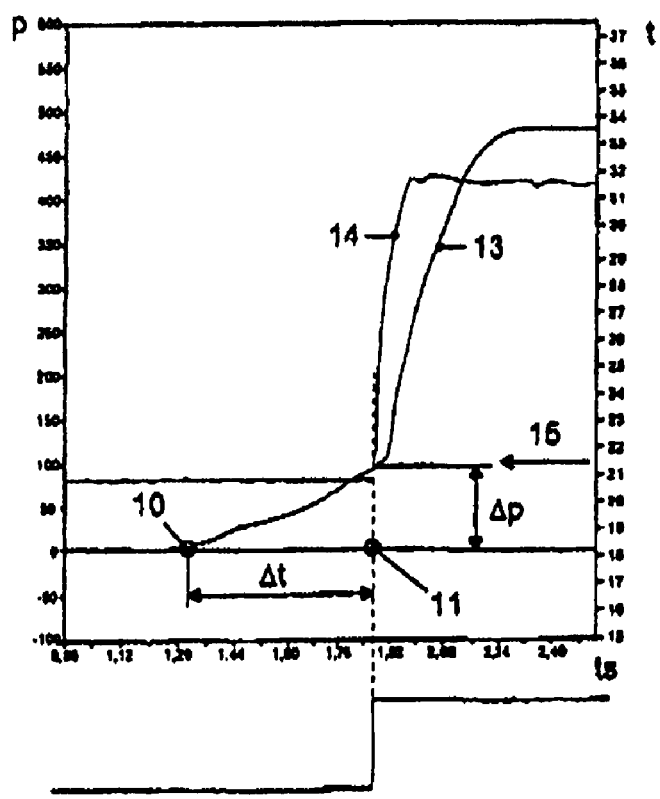
FIG. 3 shows a diagram of the pressure and temperature profile over time produced on the basis of the measurement data ascertained with the first exemplary embodiment as shown in FIG. 2.

The diagram shown in FIG. 3 was produced on the basis of measurement data ascertained with the arrangement of sensors in the cavity 9 as shown in FIG. 2. In this diagram, the time $t_s$ in seconds is indicated on the y axis and the pressure p is indicated on the x axis on the left and the temperature (abstract) is indicated on the x axis on the right, with a curve 13 reproducing the mold internal pressure profile and a curve 14 reproducing the mold wall temperature profile. At a point of intersection of the two curves, the pressure value at the point in time of the rise in temperature is indicated by an arrow 15, i.e. an automatic calculation of a shear stress takes place on the basis of $\Delta p$. The automatic calculation of a shear rate takes place on the basis of $\Delta t$.

Figure 4:
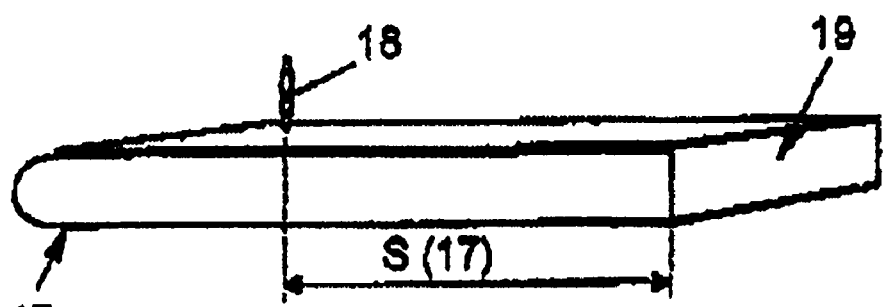
FIG. 4 shows as a second exemplary embodiment a schematic representation of a cavity of an injection mold with only one wall temperature sensor.

Schematically represented in FIG. 4 as a second exemplary embodiment is a cavity 17, which only has one mold wall temperature sensor 18, which is arranged at a distance S (17) from the entry of the melt (sprue 19).

Figure 2A:
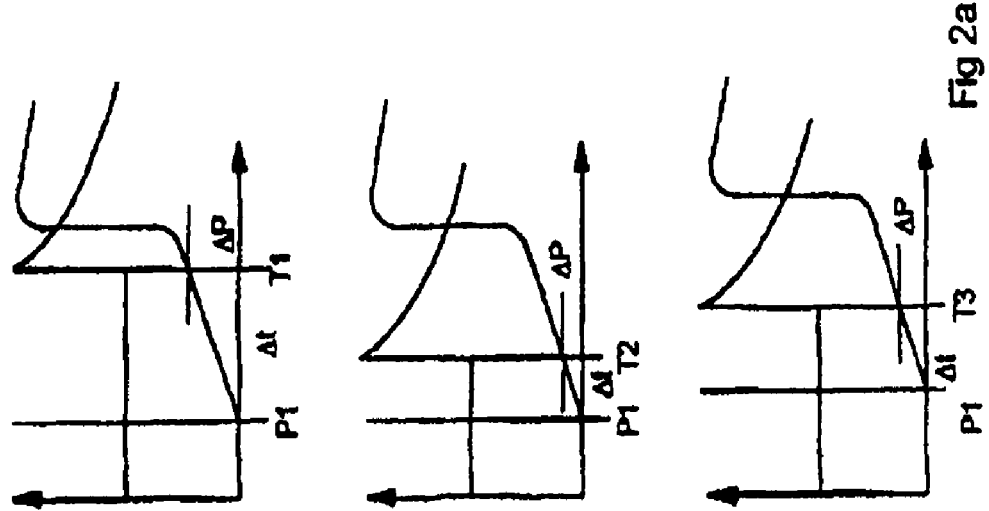
FIG. 2a shows a schematic representation of various arrangements of pressure and temperature sensors in a cavity with associated diagrams of the pressure and temperature profiles over time.
Figure 2A:
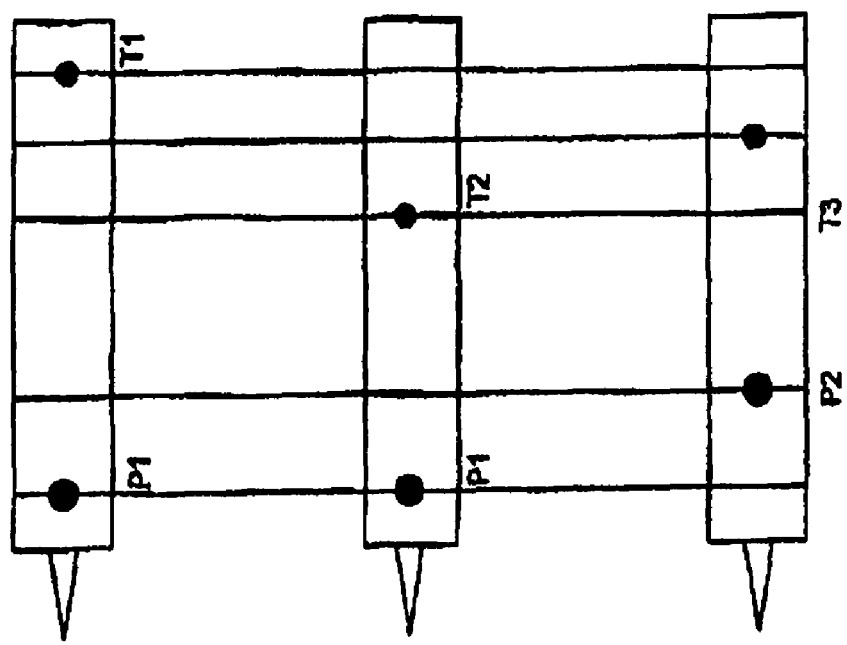

The method according to the invention for ascertaining the viscosity profile of a melt in a cavity of an injection mold of an injection molding machine for monitoring, documenting and/or controlling the latter proceeds as follows:

On the basis of the first exemplary embodiment as shown in FIG. 2, during the injection phase of the melt flowing into the cavity 9 by way of the nozzle 2 of the injection molding machine P, the viscosity of said melt is determined by ascertaining the individual quotients for this from the respective shear stresses and shear rates on the basis of the pressure differences occurring in the cavity 9 and the geometry (H×W×total length of the cavity 9). With reference to the exemplary embodiment shown in FIG. 2, this means that the mold internal pressure sensor 10 in the vicinity of the entry of the melt measures the pressure as the melt enters. As soon as the melt reaches the mold wall temperature sensor 11, a pressure measurement again takes place and the measured pressure difference corresponds exactly to the pressure value that prevails at the point in time of the rise in temperature shown in FIG. 3. A second pressure value is not necessary here, since the pressure difference between the atmospheric pressure (1 bar) and this value is assumed. The advantage of this method is also that the temperature sensor 11 can be used at the same time for automatically switching over to follow-up pressure. Moreover, however, the temperature sensor 11 can be situated anywhere in the course of the melt flow. This is illustrated in particular by FIG. 2a, in which a different arrangement of the pressure sensor 10 and the temperature sensor 11 is shown in three exemplary embodiments. Alongside are the corresponding diagrams analogous to FIG. 3. Irrespective of where the pressure sensor 10 or the temperature sensor 11 is situated, the shear stress $\Delta p$ and the shear rate $\Delta t$ are ascertained when the temperature sensor 11 is reached, and the viscosity value is calculated from this will. If this value lies at or near a predetermined value, nothing needs to be changed for the injection molding process. If, however, this value changes, the injection molding process can be changed, for example with respect to the temperature of the melt and/or the pressure or similar parameters, until the desired viscosity value is again ascertained.

In comparison with the first exemplary embodiment, measuring with the second exemplary embodiment as shown in FIG. 4 constitutes a simplification, since only one mold wall temperature sensor 18 is arranged in the course of the flow path of the melt. Either the pressure differences in the hot runner system and/or in the nozzle 6 of the injection molding machine P and/or the pressure differences in the hydraulic system are used here to calculate the respective shear stresses. Serving as a basis for the calculation of the shear rates is the distance S (17) from the sprue 19 of the mold part and the position of the mold wall temperature sensor 18.

The advantage of this method is that the melt pressures in the hot runner and in the machine nozzle represent true pressure values that do not have to be converted, while the hydraulic pressure has to be converted to true pressure values in accordance with the cross section of the hydraulic system and the cross section of the screw cylinder. The least expensive method is, however, that of measuring the hydraulic pressure, since, by contrast with melt pressure measurement, no additional sensor has to be installed for this in the machine nozzle or in the hot runner because the hydraulic pressure is always measured and used for controlling the machine. On the other hand, this method is also the least accurate because of the friction losses.

The viscosity profile is finally obtained from the various individual shear stresses and shear rates.

The first exemplary embodiment has particularly proven to be successful in practice. Here, as specified, the viscosity is ascertained and monitored in a known manner, it being possible for the viscosity profile ascertained in this way also at the same time to be documented and controlled.

In principle, different viscosities are undesired, since they lead to different properties of the parts. Causes of different viscosities are either different process conditions or different material properties (batch fluctuations). It is therefore also possible to use the method and the device according to the invention for carrying out checks on incoming material.

The invention claimed is:

1. A method for determining the viscosity of a melt in an injection mold of an injection molding machine, comprising the step of determining the viscosity of a melt when in the injection mold as a function of the respective quotients of shear stress and shear rate determined on the basis of pressure differences ($\Delta p$), the geometry of the cavity (1.1; 9; 17; 20) and the flow rate ($\Delta t$) of the melt.

2. The method as claimed in claim 1, wherein the viscosity is ascertained by at least one mold internal pressure sensor (10) and/or at least one mold wall temperature sensor (11).

3. The method as claimed in claim 2, wherein the pressure difference ($\Delta p$) of the pressure ascertained by the mold internal pressure sensor (10) at it when the melt arrives and at the mold wall temperature sensor (11) when the melt arrives is used for the shear stress and the time ($\Delta t$) that the melt needs to pass from the mold internal pressure sensor (10) to the mold wall temperature sensor (11) is used for ascertaining the flow rate.

4. The method as claimed in claim 1, wherein the viscosity is ascertained on the basis of at least one mold wall temperature sensor (18) provided in the flow path of the melt in the region of a cavity (17) of the injection mold.

5. The method as claimed in claim 4, wherein the pressure differences ($\Delta p$) in an injection nozzle (6) of the injection molding machine (P) are used as a basis for determining the respective shear stresses and the distance (S17) or the time between the entry of the melt (sprue 19) into the cavity (17) and the position of the mold wall temperature sensor (18) is used for determining the shear rates ($\Delta t$).

6. The method as claimed in claim 4 wherein the pressure differences ($\Delta p$) in a hydraulic system (7) of the injection molding machine (P) and/or in a hot runner system are used for determining the shear rates ($\Delta t$).

7. The method as claimed in claim 1, wherein the viscosity is ascertained in a way analogous to the measuring method of a rheometer on the basis of at least two spaced-apart mold internal pressure sensors (21, 22) introduced into a cavity (20) of the injection mold (1) of the injection molding machine (P).

8. The method as claimed in claim 7, wherein the pressure difference ($\Delta p$) is ascertained by the two mold internal pressure sensors (21, 22) and the shear stress is ascertained from this and from the time ($\Delta t$) that the melt needs to pass between the two mold internal pressure sensors (21, 22) and the geometry of the cavity (20).

9. The method as claimed in claim 1, wherein the pressure differences ($\Delta p$) during an injection phase of the melt are ascertained indirectly by measuring forces which are applied by elements of units to force the melt into a cavity of the injection mold.

10. A device for determining the viscosity of a melt in an injection molding machine wherein at least one mold internal pressure sensor and/or mold wall temperature sensor (10, 11, 18, 21, 22) is provided for establishing a viscosity of a melt in at least one cavity (1.1, 9, 17, 20) of an injection mold (1) of an injection molding machine (P) and can be used for determining the pressure differences that can be ascertained during a phase of injecting the melt into the at least one cavity (1.1, 9, 17, 20) and, by way of the geometry of the at least one cavity (1.1, 9, 17, 20), the respective quotients for the viscosity from the respective shear stresses and shear rates.

11. The device as claimed in claim 10, wherein a cavity (9) of the at least one cavity is assigned at least one mold internal pressure sensor (10) and/or at least one mold wall temperature sensor (11).

12. The device as claimed in claim 11, wherein the mold internal pressure sensor (10) is provided in the vicinity of the entry of the melt (sprue 19) into the cavity (9) and the mold wall temperature sensor (11) is provided in the following course of the flow path (S9) of the melt.

13. The device as claimed in claim 11, wherein the mold wall temperature sensor (11) is provided in the vicinity of the end of the flow path of the melt.

14. The device as claimed in claim 10, wherein a cavity (17) of the at least one cavity is assigned at least one mold wall temperature sensor (18) arranged on a cavity wall at a distance (S17) from an entry of the melt (sprue 19) and a pressure sensor is assigned to the injection nozzle (6) of the injection molding machine (P).

15. The device as claimed in claim 10, wherein a hydraulic system (7) of the injection molding machine (P) and/or a hot runner is assigned a pressure sensor.

16. The device as claimed in claim 10, wherein the viscosity is determined in a way analogous to the measuring method of a rheometer by at least two mold internal pressure sensors (21, 22) assigned to a cavity (20) of the at least one cavity of the injection mold (19) of the injection molding machine (P) at a distance (S20) from one another.

* * * * *